United States Patent
Lemonds et al.

(10) Patent No.: US 9,260,368 B2
(45) Date of Patent: Feb. 16, 2016

(54) PROCESS FOR PRODUCING MMA AND/OR MAA FROM ACETONE CYANOHYDRIN AND SULFURIC ACID

(71) Applicant: Rohm and Haas Company, Philadelphia, PA (US)

(72) Inventors: Andrew M. Lemonds, Lake Jackson, TX (US); Minh N. Ngo, Philadelphia, PA (US); Muhunthan Sathiosatham, Chalfont, PA (US); Donald Lee Zolotorofe, Ivyland, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/430,648

(22) PCT Filed: Sep. 9, 2013

(86) PCT No.: PCT/US2013/058679
§ 371 (c)(1),
(2) Date: Mar. 24, 2015

(87) PCT Pub. No.: WO2014/051971
PCT Pub. Date: Apr. 3, 2014

(65) Prior Publication Data
US 2015/0259272 A1    Sep. 17, 2015

Related U.S. Application Data

(60) Provisional application No. 61/707,394, filed on Sep. 28, 2012.

(51) Int. Cl.
| | |
|---|---|
| *C07C 51/06* | (2006.01) |
| *C07C 67/20* | (2006.01) |
| *C07C 303/24* | (2006.01) |
| *C07C 231/06* | (2006.01) |
| *C07C 231/12* | (2006.01) |
| *C07C 67/08* | (2006.01) |

(52) U.S. Cl.
CPC ............... *C07C 51/06* (2013.01); *C07C 67/08* (2013.01); *C07C 67/20* (2013.01); *C07C 231/06* (2013.01); *C07C 231/12* (2013.01); *C07C 303/24* (2013.01)

(58) Field of Classification Search
CPC .................... C07C 51/08; C07C 57/04
See application file for complete search history.

(56) References Cited

U.S. PATENT DOCUMENTS

| | | | |
|---|---|---|---|
| 4,529,816 A | | 7/1985 | DeColibus et al. |
| 6,075,162 A | * | 6/2000 | Kida ............... C01C 3/0241 558/332 |
| 7,253,307 B1 | * | 8/2007 | Carlson, Jr. ......... C07C 51/06 562/526 |
| 7,582,790 B2 | | 9/2009 | Schladenhauffen et al. |
| 8,143,434 B2 | | 3/2012 | Gropp et al. |
| 2003/0208093 A1 | | 11/2003 | Carlson, Jr. et al. |
| 2011/0318515 A1 | * | 12/2011 | Dubois et al. ............ 428/36.9 |

* cited by examiner

*Primary Examiner* — Karl J Puttlitz
(74) *Attorney, Agent, or Firm* — Edward L. Brant

(57) ABSTRACT

A multistage process for the preparation of methacrylic acid and esters thereof via the hydrolysis of ACH, cracking the hydrolysis products, and converting the cracked products to the desired acid or ester, wherein the average temperature in the first hydrolysis reactor is from 55 C to 70 C.

10 Claims, No Drawings

PROCESS FOR PRODUCING MMA AND/OR MAA FROM ACETONE CYANOHYDRIN AND SULFURIC ACID

CROSS-REFERENCE TO RELATED APPLICATIONS

This application claims priority from provisional application Ser. No. 61/707,394, filed Sep. 28, 2012, which is incorporated herein by reference in its entirety.

BACKGROUND OF THE INVENTION

The invention relates to high yield production processes for methacrylic acid ("MAA") and methacrylate esters, such as methyl methacrylate ("MMA").

A number of commercial processes are used to prepare MMA. In one such process, MMA is prepared from acetone cyanohydrin ("ACH"). The process is described in U.S. Pat. No. 4,529,816 ("816"). In this process, ACH is (1) hydrolyzed by sulfuric acid to produce alpha-hydroxyisobutyramide ("HIBAM") and its sulfate ester, alpha-sulfatoisobutyramide ("SIBAM"); (2) the HIBAM and SIBAM are thermally converted, or cracked, to 2-methacrylamide ("MAM") and a small amount of methacrylic acid ("MAA"); which are then (3) esterified with methanol to produce MMA. Residual HIBAM is esterified to methyl alpha-hydroxyisobutyrate ("MOB"). In step (2) of the reaction, the conversion of SIBAM to MAM occurs more readily than the conversion of HIBAM to MAM. In order to facilitate the thermal conversion of HIBAM to MAM, both heat and increased residence time must be provided. A decrease in thermal conversion to desired products results in a decreased overall yield for the process. The process of preparing MAA can be the same as that used to prepare MMA, except that instead of esterifying MAM and MAA with methanol, water is added to the MAM and MAA mixture to convert the MAM to MAA.

One means of employing this chemistry is disclosed in US 20030208093. In that process, one to five hydrolysis reactors are employed to feed an integrated follow-on system that completes the cracking and subsequent steps of the process.

In the ACH hydrolysis process, reaction yield can be lost to the thermal decomposition of ACH to acetone and HCN. In this strongly acidic environment, these immediate decomposition products are also consumed. For example, acetone reacts with sulfuric acid to form acetone mono- and disulfonic acids (AMSA and ADSA) and water. HCN hydrolyzes to formamide, which in turn decomposes to equivalents of CO and $NH_3$ (forming ammonium bisulfate with sulfuric acid).

The ACH hydrolysis process is strongly exothermic; heats of mixing and reaction drive up temperatures, resulting in additional ACH decomposition. Managing this problem requires efficient mixing at the point of ACH introduction to quickly dissipate heat, and cooling to minimize the reaction temperature. The latter, however, is constrained by increasing viscosity and the solidification, or "salting," of the reaction mixture at low temperatures. The term "salting" is commonly used as it infers the acid-base interactions that take place between sulfuric acid and the amide species present. As a result, ACH hydrolysis processes are typically operated just above the salting temperature for practical management of viscosity and to avoid salting.

While this approach of minimizing hydrolysis temperatures within practical limits is straightforward, it does not provide a complete rationale for improving the overall ACH to MAM process yield, especially for multi-reactor hydrolysis systems. Successful improvements ideally would 1) achieve hydrolysis reactor compositions capable of lower respective operating temperatures and 2) give improved reaction product overall yield through the thermal cracking step. Rationalized paths to these objectives require a thorough understanding of the process/composition/property interrelationships. Unfortunately, these are highly multivariate and, in terms of definitive predictive ability, remain poorly understood.

Ensuring net gains in an MMA process from hydrolysis improvements requires hydrolysis compositions that convert in a net positive overall yield through the thermal cracking step. This latter step, again, converts HIBAM to the desired process intermediate MAM. Due to common HIBAM levels, this step cannot be foregone, yet its conditions are severe and contribute to the bulk of yield losses in the MMA process. Therefore, hydrolysis improvements must strike a balance between value gained from HIBAM versus the other three hydrolysis yield components SIBAM, MAM, and MAA. Hypothetically speaking, an improvement that selectively increases HIBAM hydrolysis yield could result in a reduced overall yield post-thermal cracking.

The MMA and MAA markets are extremely cost sensitive. A slight improvement in process yield can result in a significant market advantage. There is a need for an improved yield commercial process of preparing MMA and/or MAA.

SUMMARY OF THE INVENTION

The invention is such a process for the preparation of methacrylic acid and esters thereof, the process comprising:
(i) continuously feeding a first raw material comprising acetone cyanohydrin and a second raw material comprising sulfuric acid, oleum or mixtures thereof into a first hydrolysis reactor;
(ii) continuously feeding the effluent stream of the first hydrolysis reactor and a third raw material comprising acetone cyanohydrin into a second hydrolysis reactor;
(iii) continuously feeding the effluent stream of the second hydrolysis reactor and a fourth raw material comprising acetone cyanohydrin into a third hydrolysis reactor;
(iv) continuously hydrolyzing the hydrolyzable contents of said each hydrolysis reactor to form a first, second, and third hydrolysis product, respectively, each product comprising alpha-sulfatoisobutyramide and alpha-hydroxyisobutyramide; and
(v) continuously feeding the effluent stream of the third hydrolysis reactor to a cracking system,
wherein the average temperature in the first reactor is from 55° C. to 70° C.

Surprisingly, the yield of ACH hydrolysis products is improved by the process of the invention. The yield of downstream cracking products also is unexpectedly improved.

DETAILED DESCRIPTION OF THE INVENTION

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The process of the invention can be used to prepare methacrylic acid and esters thereof via the hydrolysis of ACH with sulfuric acid. ACH and commercial methods for its preparation are well known to those skilled in the art. The sulfuric acid serves as both a specific reactant and a solvent for the reaction. Using sulfuric acid at concentrations of greater than 95% is preferred. In an alternative embodiment, oleum or a combination of sulfuric acid and oleum may be used in place of sulfuric acid. Advantageously, the ACH and sulfuric acid are fed to the process in the liquid phase. In one embodiment of the invention, the total amount of sulfuric acid employed is at least 1.4 moles per mole of ACH, and preferably is from 1.5 to 1.8 moles of acid per mole of ACH. It is preferable to use ACH that has low levels of water and other impurities in the hydrolysis step.

One example of an integrated process of making MAA and/or methacrylate esters from ACH is described in US 20030208093. As in that process, the first stage of producing MAA and/or methacrylate esters from ACH involves hydrolysis of the ACH in a hydrolysis system; the general chemistry of the hydrolysis process for both MAA and methacrylate esters may be very similar. The ACH is hydrolyzed in a hydrolysis system to produce a hydrolysis mixture that contains alpha-sulfatoisobutyramide ("SIBAM") and alpha-hydroxyisobutyramide ("HIBAM"). ACH and a molar excess of sulfuric acid are fed into the hydrolysis reactors. The hydrolysis system of the invention employs multiple reactors connected in series and also employs multiple reactant addition points. In the hydrolysis reaction, anhydrous conditions are preferred to minimize the formation of HIBAM, which is more difficult than SIBAM to convert to methacrylamide (MAM).

In one embodiment of the invention, the hydrolysis reaction for all of the processes can be combined in an "integrated hydrolysis system." Thus, rather than having parallel hydrolysis trains for MAA and methacrylate esters that involve at least two lines of essentially the same equipment, the process of one embodiment of the invention needs only one integrated hydrolysis system. This common integration scheme can continue through the cracking step and up to the reaction step, as the reaction steps for methacrylate esters and MAA differ. This sharing of equipment results in a substantial cost savings to the manufacturer via reduced capital costs, reduced personnel needs, and reduced long-term operating costs. Also, the manufacturer may achieve additional savings due to the economy of scale achieved by combining the processes.

In one embodiment of the invention, three to five hydrolysis reactors are connected in series to form an integrated hydrolysis system for both MAA and methacrylate esters production. Any reactors suitable for conducting hydrolysis reactions that are known in the art may be used such as, for example, a continuous stirred tank reactor, a tubular reactor as disclosed in U.S. Pat. No. 7,582,790, or a "loop reactor" as disclosed in U.S. Pat. No. 8,143,434. However, such reactors should be resistant to the corrosive effects of the reaction, thus the hydrolysis reactors and reactor ancillaries preferably may be constructed of material resistant to corrosion. The term "reactor ancillaries" means any and all secondary equipment, such as exchangers, instrumentation, mixers and pumps, and associated piping that is connected to the reactor. The term "associated piping" includes, but is not limited to, feed lines, bottoms lines, overflow lines, vent lines, inhibitor addition lines, and oxygen addition lines.

Suitable materials of construction that are resistant to corrosive effects include but are not limited to: stainless steel (e.g., 300 series, 904L, 6-moly), HASTELLOY (e.g., B, B-2, B-3, C-22, and C-276), commercially available tantalum, and zirconium materials, and alloys thereof. In some embodiments, the manufacturer may reduce construction costs by utilizing covered base materials. "Covered base materials" are materials that generally are thought not to be corrosion resistant, such as carbon steel, combined with a covering or coating capable of resisting corrosion such as glass, epoxy, elastomer, fluoropolymer (e.g., TEFLON), or one of the above-listed metals. Covered base materials are constructed by placing a covering or coating capable of resisting corrosion over, and optionally bonding the covering to, the base metal. The covering prevents base-metal contact with the process stream. Covered base-metal construction is especially preferred for large-diameter piping (3.8 cm or larger nominal diameter) and for heat exchanger tubes in high fluid-velocity service (fluid velocity of 0.15 meter/second or more) and other components, where significant metal thickness (3 mm or more metal thickness) may be used to provide structural strength. The materials described above such as stainless steel (e.g., 300 series, 904L, 6-moly), HASTELLOY alloys, tantalum, and zirconium, and covered base-metal materials are hereinafter referred to as "corrosion resistant material."

Generally speaking, the hydrolysis temperature can be lowered as the ratio of sulfuric acid to ACH increases. Temperatures can be controlled through various means known in the art, such as use of internal cooling coils or recirculation of a portion of the reactor contents through external heat exchangers. The temperature can be held constant throughout the hydrolysis reaction or it can be changed during the course of the reaction, especially when multiple hydrolysis reactors are used in series. If more than one reactor is used, preferably the temperature of the first reactor ranges from 55° C. to 70° C., and the temperature of subsequent reactors ranges from 80° C. to 105° C. In one embodiment of the invention wherein 3 hydrolysis reactors are employed, the temperature of the second reactor preferably is from 80° C. to 95° C., and the temperature of the third reactor preferably is from 100° C. to 105° C.

Viscosity and salting are affected by the composition of the hydrolysis mixture. In general, the more ACH added relative to sulfuric acid, the higher the viscosity and salting temperature. Specifically, viscosity and salting are determined by the composition matrix of sulfuric acid, HIBAM, SIBAM, MAM, MAA, AMSA, ADSA, ammonium bisulfate, and other components, having mainly to do with the acid-amide interactions. The composition is of course dictated by the process conditions: feed composition (neat sulfuric acid or a preceding hydrolysis reactor effluent), mole ratio, reaction temperature, residence time, and mixing uniformity, and other factors. Advantageously, the process is operated under conditions such that substantially no salt crystals are formed.

The reaction time may vary from one minute to an hour. In one embodiment of the invention, the hydrolysis reaction advantageously is conducted for a sufficient time to maximize the yield of MAM, SIBAM, and HIBAM. In one embodiment of the invention, in a system with 3 hydrolysis reactors, the residence time in the first hydrolysis reactor is from 18 to 31 minutes, the residence time in the second hydrolysis reactor is from 5 to 18 minutes, and the residence time in the third hydrolysis reactor is from 4 to 17 minutes.

In one embodiment of the invention, ACH is fed such that, in a system with 3 hydrolysis reactors, from 30 to 55 weight % of the ACH is fed to the first hydrolysis reactor, from 20 to 40 weight % of the ACH is fed to the second hydrolysis reactor, and from 10 to 40 weight % of the ACH is fed to the third hydrolysis reactor, with the proviso that the total amount of ACH fed is 100%. In another embodiment, the amount of ACH fed to each of the 3 hydrolysis reactors is such that from 33 to 50 weight % of the ACH is fed to the first reactor, from 30 to 33 weight % of the ACH is fed to the second reactor, and from 20 to 33 weight % of the ACH is fed to the third reactor.

One or more polymerization inhibitors may be added to the hydrolysis system to prevent polymerization. Suitable locations for adding the inhibitor to the hydrolysis system are well known in the art and include, but are not limited to, the raw material streams upstream of the hydrolysis system, the hydrolysis reactor(s) itself and its reactor ancillaries. If multiple reactors are used and connected in series, then it is preferable to add the inhibitor to the first reactor. However, different inhibitors may be added to each reactor individually if desired via one inhibitor addition point or multiple inhibitor addition points.

The next step in one embodiment of the process of the invention is cracking the hydrolysis mixture in a cracking train. Cracking is known to those skilled in the art. Cracking can be accomplished as described in US 2003/0208093.

The cracker reactor effluent mixture may be transferred to at least one reactor, wherein said mixture is either contacted with methanol and reacted by methods known in the art to produce an esterification mixture that includes, but is not limited to, predominantly MMA, with lesser amounts of MAA, MAM, methyl-alpha-methoxyisobutyrate ("alpha-MEMOB"), methyl-beta-methoxyisobutyrate ("beta-MEMOB"), MOB, methanol, mineral acids and MMA/MAA copolymer, or the cracker reactor effluent mixture may be contacted with water and reacted by methods known in the art to produce a mixture that includes predominantly MAA. The reaction conditions are not critical and can be varied over a wide range. The only requirement is that the conditions be mild enough such that side reactions leading to degradation products do not occur to an unacceptable extent. The reaction is typically run at a temperature ranging from 85° C. to 180° C. The temperature can be maintained at one value or changed during the course of the reaction. The esterification reaction may be run in a continuous flow stirred tank reactor or a plug flow reactor. Alternatively, the esterification reaction may be run in one or more reactors, which, may be connected in parallel or in series.

Purification and recovery of the reaction products can be accomplished according to methods well known to those skilled in the art.

SPECIFIC EMBODIMENTS OF THE INVENTION

The following examples are given to illustrate the invention and should not be construed as limiting its scope.

Example 1

Acetone cyanohydrin (ACH) (>99.99 wt. % assay) is hydrolyzed with sulfuric acid (99.2 wt. % assay) in three continuous-flow, stirred-tank reactors in a series arrangement. The reactor system comprises cylindrical, jacketed glass reaction flasks ("resin kettles"): a 1,000 ml first reactor, a 500 ml second reactor, and a 1,000 ml third reactor. Each contains a set of internal mixing baffles (four baffles per reactor) and 2-3 mixing impellers (two-blade, 45 deg. pitch). Sulfuric acid, 1,830 g/hr, is fed to the first reactor, and ACH, 1,073 g/hr in total, is fed to the first (50% of total ACH), second (30%), and third (20%) reactors. A polymerization inhibitor feed mixture, 15 wt. % phenothiazine (PTZ, 99%) in acetone (>99.99%), is admixed with the ACH main feed to provide 300 ppm PTZ in the ACH. Operating pressure is 1 atm absolute. Temperatures and working volumes are as follows:

TABLE 1

Example 1 Conditions

| | Hydrolysis Reactor 1 | Hydrolysis Reactor 2 | Hydrolysis Reactor 3 |
|---|---|---|---|
| Temperature (° C.) | 65 | 90 | 100 |
| Working volume (ml) | 580 | 382 | 339 |
| Mixing power (hp/mgal) | 4.24 | 13.5 | 4.24 |

The final hydrolysis reaction product (Hydrolysis Reactor 3 effluent) is analyzed by 1H nuclear magnetic resonance spectroscopy (1H NMR). Analytical samples are prepared by mixing 3.3 g methane sulfonic acid, the internal standard, with 10 g of product sample at 80° C. for 3 hours. A 0.05 ml aliquot of each analytical sample mixture is then added to 0.5 ml nitromethane in an NMR vial. The hydrolysis yield is defined as:

$$\text{Hydrolysis yield (\%)} = \frac{n_{MAM}^{out} + n_{SIBAM}^{out} + n_{HIBAM}^{out} + n_{MAA}^{out}}{n_{ACH}^{in}} \times 100$$

where
$n_{MAM}^{out}$=MAM molar flow rate in the hydrolysis reactor effluent
$n_{SIBAM}^{out}$=SIBAM molar flow rate in the hydrolysis reactor effluent
$n_{HIBAM}^{out}$=HIBAM molar flow rate in the hydrolysis reactor effluent
$n_{MAA}^{out}$=MAA molar flow rate in the hydrolysis reactor effluent
$n_{ACH}^{in}$=ACH molar flow rate in the hydrolysis reactor feed The steady-state hydrolysis reaction yield (Hydrolysis Reactor 3 effluent) is 95.8% with a standard error of 0.14% from 211 analyzed samples collected over 12 replicate experiments.

Example 2

The hydrolysis product of Example 1 is fed directly to a thermal conversion apparatus comprising four plug flow tubular reactors in series. The reactors are steam-heated, single-shell and single-tube heat exchangers. The reaction is conducted on the tube side, which is 0.25-in O.D. Hastelloy HC-276 tubing. The operating pressure is 65 psig. Temperatures and working volumes are as follows:

TABLE 2

Example 2 Conditions

|  | Thermal Conversion Reactor 1 | Thermal Conversion Reactor 2 | Thermal Conversion Reactor 3 | Thermal Conversion Reactor 4 |
|---|---|---|---|---|
| Temperature (° C.) | 122 | 156 | 156 | 100 |
| Reactor volume (ml) | 7.5 | 11.2 | 22.0 | 15.0 |

The final thermal conversion product (Thermal Conversion Reactor 4 effluent) is analyzed by 1H NMR. Analytical samples are prepared by mixing 4.5 g methane sulfonic acid, the internal standard, with 10 g of product sample at 80° C. for 3 hours. A 0.05 ml aliquot of each analytical sample mixture is then added to 0.5 ml nitromethane in an NMR vial. The thermal conversion yield is defined as:

$$\text{Thermal conversion yield (\%)} = \frac{n_{MAM}^{out} + n_{MAA}^{out}}{n_{ACH}^{in}} \times 100$$

where
$n_{MAM}^{out}$=MAM molar flow rate in the cracking reactor effluent
$n_{MAA}^{out}$=MAA molar flow rate in the cracking reactor effluent
$n_{ACH}^{in}$=ACH molar flow rate in the hydrolysis reactor feed The steady-state thermal conversion yield (Thermal Conversion Reactor 4) is 90.6% with a standard error of 0.14% from 302 analyzed samples collected over 15 replicate experiments.

The ACH is fed to all three hydrolysis reactors. The third reactor is equipped with heat removal capability, and does not use a recycle stream. All respective hydrolysis reaction temperatures are lowered compared to the prior art. The staging of the ACH feed, as described for the invention, lowers the hydrolysis reaction residence time of the ACH portion that is shifted towards the end of the hydrolysis process. Thus, the time for the corresponding SIBAM that is formed from the later staged ACH to convert to MAM is reduced. We have found surprisingly, despite this lowered hydrolysis residence time, that the described three-stage process increases productivity and yield through both the hydrolysis and cracking systems. Specifically and for a given feed rate, the absolute rate of SIBAM+HIBAM+MAM+MAA from hydrolysis and MAM+MAA from cracking increases. Also surprisingly, the conditions of the three-stage process decrease the minimum operating temperature of the third hydrolysis stage.

Therefore, the process of the invention surprisingly and simultaneously improves the ACH hydrolysis and cracking reaction productivity and yield for the use of a fixed-asset hydrolysis system (reactor vessel count, order, size, and volume) and for a fixed overall raw material feed (i.e., fixed overall ACH and sulfuric acid feed). This invention enables economically significant gains to be obtained with minimal modification, effectively limited to piping and heat exchange hardware, to existing hydrolysis reaction systems. Such an improvement is valuable for extending the cost competitiveness of existing commercial scale MMA plants that employ ACH and sulfuric acid-based technology, which continue to supply the market today.

What is claimed is:

1. A process for the preparation of methacrylic acid and esters thereof, the process comprising:
    (i) continuously feeding a first raw material comprising acetone cyanohydrin and a second raw material comprising sulfuric acid, oleum or mixtures thereof into a first hydrolysis reactor to obtain a first effluent stream of the first hydrolysis reactor;
    (ii) continuously feeding the effluent stream of the first hydrolysis reactor and a third raw material comprising acetone cyanohydrin into a second hydrolysis reactor to obtain a second effluent stream of the second hydrolysis reactor;
    (iii) continuously feeding the effluent stream of the second hydrolysis reactor and a fourth raw material comprising acetone cyanohydrin into a third hydrolysis reactor to obtain a third effluent stream of the third hydrolysis reactor;
    (iv) continuously hydrolyzing the hydrolyzable contents of said each hydrolysis reactor to form a first, second, and third hydrolysis product, respectively, each product comprising alpha-sulfatoisobutyramide and alpha-hydroxyisobutyramide; and
    (v) continuously feeding the effluent stream of the third hydrolysis reactor to a cracking system; and
    (vi) continuously cracking the effluent stream of the third hydrolysis reactor in said cracking system to form a cracking product comprising methacrylamide; and
        (viia) continuously feeding said cracking product and water to an acid formation reactor; and
        (viiia) continuously reacting said cracking product and said water in said acid formation reactor to form an acid formation product comprising methacrylic acid;
    or
        (viib) continuously feeding said cracking product and an alcohol to an ester formation reactor; and
        (viiib) continuously reacting said cracking product and said alcohol in said ester formation reactor to form an ester formation product comprising an ester of methacrylic acid;
    or
        (viic) continuously feeding a first portion of said cracking product and water to an acid formation reactor, while continuously feeding a second portion of said cracking product and an alcohol to an ester formation reactor; and
        (viiic) continuously reacting said first portion of said cracking product and said water in said acid formation reactor to form an acid formation product comprising methacrylic acid; and continuously reacting said second portion of said cracking product and said alcohol in said ester formation reactor to form an ester formation product comprising an ester of methacrylic acid,
    wherein the average temperature in the first reactor is from 55° C. to 70° C.

2. The process of claim 1 wherein the product of the hydrolysis substantially remains in solution while in the reactors.

3. The process of claim 1 wherein the average temperature of the second hydrolysis reactor is from 80° C. to 105° C.

4. The process of claim 1 wherein the average temperature of the third hydrolysis reactor is from 100° C. to 105° C.

5. The process of claim 1 wherein the process is operated under conditions such that substantially no salt crystals are formed.

6. The process of claim 1 wherein the average temperature of the second hydrolysis reactor is from 80° C. to 105° C., and the average temperature of the third hydrolysis reactor is from 100° C. to 105° C.

7. The process of claim 1 wherein from 20 to 40 weight % of the ACH is fed to the second hydrolysis reactor.

8. The process of claim 1 wherein from 10 to 40 weight % of the ACH is fed to the third hydrolysis reactor.

9. The process of claim 1 wherein the amount of ACH fed to each of the 3 hydrolysis reactors is such that from 33 to 50 weight % of the ACH is fed to the first reactor, from 30 to 33 weight % of the ACH is fed to the second reactor, and from 20 to 33 weight % of the ACH is fed to the third reactor.

10. The process of claim 1 wherein, if said cracking system comprises two or more cracking reactors, in parallel, then a first portion of a cracking product from each of said cracking reactors and water is continuously fed to said acid formation reactor and a second portion of a cracking product from each of said cracking reactors and an alcohol is continuously fed to said ester formation reactor.

\* \* \* \* \*